United States Patent [19]

Elias

[11] Patent Number: 4,790,835

[45] Date of Patent: Dec. 13, 1988

[54] URINARY MALE DIAPER

[76] Inventor: Barney Elias, 500 W. State, Apt. 3D, Jacksonville, Ill. 62650

[21] Appl. No.: 56,887

[22] Filed: Jun. 3, 1987

[51] Int. Cl.[4] ................................................ A61F 5/44
[52] U.S. Cl. ..................................... 604/349; 604/351
[58] Field of Search ............... 604/347, 348, 349, 350, 604/351, 352, 353; 128/132 R

[56] References Cited

U.S. PATENT DOCUMENTS

| | | | |
|---|---|---|---|
| 713,900 | 11/1902 | Miller et al. | 604/353 |
| 2,525,238 | 10/1950 | Penska | 604/349 |
| 2,873,740 | 2/1959 | Wainwright | 604/347 |
| 3,161,197 | 12/1964 | Glas et al. | 604/352 |
| 3,648,700 | 3/1972 | Warner | 604/349 |
| 3,788,324 | 1/1974 | Lim | 604/352 |
| 4,527,988 | 7/1985 | Lutz et al. | 604/349 |
| 4,590,931 | 5/1986 | Kidwell, Jr. | 604/349 |

FOREIGN PATENT DOCUMENTS 0641521  8/1928  France .................................. 604/349

*Primary Examiner*—C. Fred Rosenbaum
*Assistant Examiner*—Mario Costantino
*Attorney, Agent, or Firm*—Shlesinger Arkwright & Garvey

[57] ABSTRACT

A male urinary diaper includes a generally tubular-shaped sheath formed from moisture resistant material with an open proximal end portion and a closed distal end portion and absorbent material positioned within the distal end portion. The distal end portion has a first portion forming an uninterrupted continuation of the distal end portion and a free flap portion forming an extension of the first portion which is discontinuous with respect to the distal end portion and circumferentially overlaps upon the first portion and has a releasable fastening element.

7 Claims, 1 Drawing Sheet

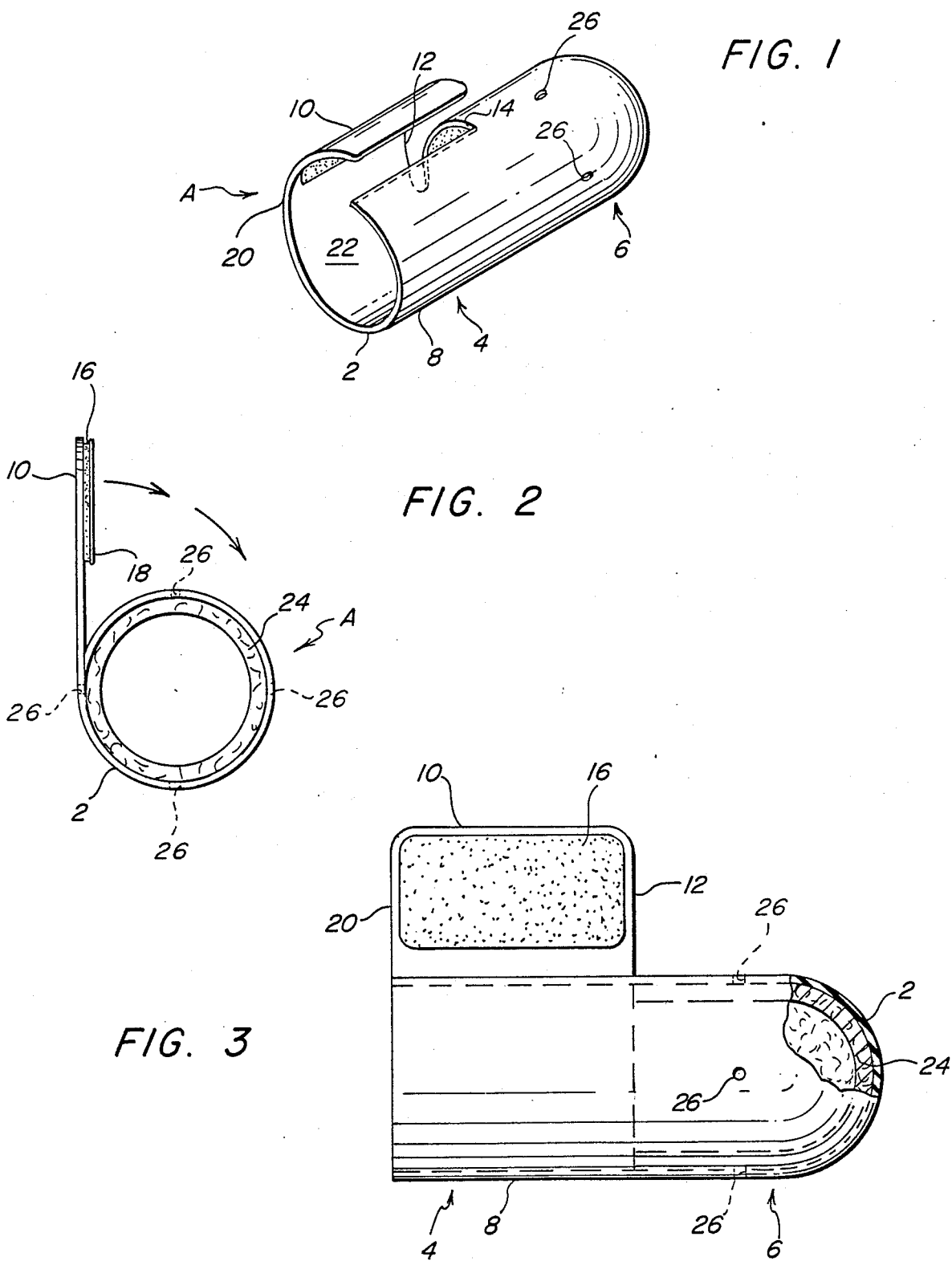

URINARY MALE DIAPER

FIELD OF THE INVENTION

This invention generally relates to a urinary diaper or shield for use by men in order to catch uncontrolled urinary discharge thereby protecting the user's clothing from staining.

BACKGROUND OF THE INVENTION

With regard to the male population, the problems associated with involuntary urinary discharge and the like have led to a variety of developments in the field of male sanitary diapers or shields.

Examples of some of these devices are disclosed by U.S. Pat. Nos. 2,891,546 to Galloway; 2,678,649 to Ghusn; 4,601,716 to Smith; 713,900 Miller; and 1,866,060 to Schmidt.

Additional devices in the form of male urinals with attached collection tubes are disclosed U.S. Pat. Nos. 3,032,038 to Swinn; 947,725 to Yates; and 3,364,932 to Beech.

One or more disadvantages can be attributed to the construction of the various devices disclosed above. Several of the devices are not self-supported thereby requiring the need for additional supporting structure. Other of the devices are overly complicated in construction or are non-adjustable thereby adding to the degree of difficulty in initially positioning and subsequently fastening the device in place Prior to use.

A further disadvantage associated with the prior art devices is the discomfort associated with the wearing of the devices.

SUMMARY AND OBJECTS OF THE INVENTION

The male urinary diaper or shield of the present invention comprises a one-piece tubular-shaped sheath of moisture resistant material having an open proximal end portion and a closed distal end portion. The proximal end portion is partially formed as an uninterrupted continuation of the distal end portion with the remainder of the proximal end portion comprising a free flap which is discontinuous with respect to the distal end portion.

The discontinuity of the free flap with respect to the distal end allows unrestricted enlargement of the open proximal end portion to facilitate initial placement of the shield over the user's penis. After being properly positioned, the free flap may be adjustably overlapped upon the remaining first portion of the proximal end portion in order to decrease the diameter of the open proximal end portion. Fastening means are provided on the inner surface of the free flap in order to securely lock the overlapping flap in the desired position.

The proximal end portion of the sheath comprising the first portion and the free flap portion essentially constitute an adjustment band having substantial width so as to evenly distribute the locking pressure exerted upon the user's penis once the free flap portion is secured in place, as opposed to localizing the locking pressure as would be the case by using a draw string or an equivalent securing arrangement.

An absorbent material is positioned within the distal end portion of the sheath in order to trap any fluid which accumulates in the closed distal end during use of the device. Aeration means are likewise provided in the distal end portion of the sheath in order to facilitate natural air drying of the absorbent material as well as to provide a degree of air circulation within the sheath during use.

It is therefore an object of the present invention to provide a urinary diaper or shield for men which is light weight and self-supporting.

Another object of the present invention is to provide a urinary diaper or shield for men which is comfortable to wear and unobtrusive due to its natural shape.

A further object of the present invention is to Provide a urinary diaper or shield for men having a free flap portion allowing selective adjustment with respect to the diameter of the open proximal end of the device facilitating initial placement and subsequent securement of the device on the user's penis.

Still a further object of the present invention is to provide a urinary diaper or shield for men which is uncomplicated in construction.

A still further object of the present invention is to provide a urinary diaper or shield for men which is inexpensive to manufacture.

The foregoing as well as other objects and advantages of this invention will appear from the following detailed description, taken in conjunction with the accompanying drawings.

DESCRIPTION OF THE DRAWINGS

FIG. 1 is a perspective view of the urinary diaper or shield of the present invention.

FIG. 2 is an end view of the device of FIG. 1

FIG. 3 is a side elevational view of the device of FIGS. 1 and 2 with a portion broken away to show the inner construction thereof.

DETAILED DESCRIPTION OF THE INVENTION

Referring to the drawings, the urinary diaper or shield A is formed from a one-piece generally tubular shaped sheath constructed of moisture resistant material 2. The moisture resistant material may be any suitable material, for instance, rubber, a plastic resin such as polyethylene, polypropylene, polyvinyl chloride, ethylene vinyl acetate or the like. The material should generally be moisture impervious and resistant to the chemical action of urine. The sheath should be semiflexible, i.e., the material is sufficiently flexible to allow the sheath to be deformed under the application of pressure but will retain its original shape when no pressure is applied thereto.

Shield A includes an open proximal end portion 4 and a closed distal end portion 6. Proximal end portion 4 includes an extension or first portion B which is an uninterrupted continuation of distal end portion 6. Proximal end portion 4 also includes a free flap portion 10 which is an uninterrupted continuation of extension 8. Free flap portion 10 is discontinuous with respect to distal end portion 6. The discontinuity of flap 10 with respect to distal end portion 6 is caused by the fact that edge 12 of flap 10 is not connected to edge 14 of distal end portion 6.

The discontinuity between flap 10 and distal end portion 6 allows flap 10 to be pulled back with respect to extension 8 to enlarge the opening of proximal end portion 4 thus facilitating placement of shield A onto the penis of the user. Once proper placement is achieved, flap 10 may be adjustably overlapped so as to rest upon extension 8 thus decreasing the diameter of open proximal end portion 4.

An adhesive layer 16 may be applied to the inner surface of flap 10 in order to provide a means for securing flap 10 to extension 8. As shown in FIG. 2, adhesive layer 16 may be provided with a removable protective cover 18. It is obvious that any other conventional fastening means may be substituted for adhesive layer 16. Flap 10 may be secured to extension 8 by snaps, buttons, Velcro, etc.

The overall width of flap 10, i.e., the distance between edge 12 and edge 20 is preferably about one half of the overall length of shield A. The relatively large width of flap 10 causes an equal distribution of pressure upon the user's penis when the shield is in place and flap 10 is secured in overlapping relationship upon extension 8. This is a distinct advantage over prior art devices using relatively thin draw strings or bands which tend to localize the pressure exerted upon the user's penis.

The continuous nature of extension 8 and flap 10 combined with the fact that flap 10 is discontinuous with respect to distal end portion 6 provides for a smooth inner contact surface 22 adjacent to the skin of the user when the device is properly positioned and secured in place. This arrangement provides additional comfort as opposed to an arrangement where the material forming the proximal end portion of a sheath or similar device is bunched up around the skin of the user during securement of the device in place.

An absorbent material, such as absorbent liner 24 is positioned within distal end portion 6 of shield A in order to absorb and bind up any fluid collected in distal end portion 6. The absorbent material may be selected from any of the well known absorbent materials, for example, cotton or any of the synthetic hydrophilic materials currently being marketed. Absorbent liner 24 may be loosely positioned in the distal end portion 6 or may be secured adjacent to the inner surface of moisture resistant material 2.

Aeration means in the form of holes 26 are provided through moisture resistant material 2 in the distal end portion 6 of shield A. Preferably, holes 26 are equally spaced around the circumference of distal end portion 6 as shown. Aeration means 26 provide some ventilation into the interior of shield A and also function to allow a degree of air drying of absorbent liner 24 once the liner has become wet.

The proximal end portion 4 has preferably a number of small breathing holes, not shown. It is also understood that the number of aeration holes 26 on the distal end portion 6 can be made.

Preferably, the overall length of the diaper is 4 inches. The proximal end portion 4 has a longitudinal dimension of 2 inches. And, the internal diameter is 1½ inches.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

What is claimed is:

1. A urinary diaper or shield for men comprising:
   (a) a one-piece generally tubular-shaped sheath formed from moisture resistant material including an open proximal end portion and a closed distal end portion,
   (b) said sheath including an inner surface and an outer surface,
   (c) a thick absorbent liner positioned within said distal end portion of said sheath in direct contact with the entire inner surface thereof,
   (d) the distal end of said sheath having a plurality of spaced aeration holes disposed on its surface and extending therethrough to permit both uniform ventilation and also air drying of the absorbent liner once it becomes wet,
   (e) said proximal end portion including a first portion forming an uninterrupted continuation of a partial circumferential section of said distal end portion, and a fee flap portion forming an uninterrupted circumferential extension of said first potion,
   (f) the free flap portion being of such a length so as to adjustably overlap upon said first portion to both close the sheath and to vary the diameter of said open proximal end portion,
   (g) the fee flap portion being discontinuous with but on closure having an edge in normal abutting relationship with the adjacent edge of the distal portion, and including means for releasably attaching said overlapping flap portion to the said first portion.

2. A urinary diaper or shield as in claim 1, wherein:
   (a) said absorbent material being in the form of an inner liner positioned adjacent to said inner surface of said sheath.

3. A urinary diaper or shield as in claim 2, wherein:
   (a) said distal end of said sheath including aeration means.

4. A urinary diaper or shield as in claim 3, wherein:
   (a) said aeration means including a plurality of circumferentially spaced holes extending through said moisture resistant material of said sheath and communicating with said absorbent material.

5. A urinary diaper or shield as in claim 1, wherein:
   (a) said flap portion including an inner surface and an outer surface, and
   (b) said means for releasably attaching said flap portion to said first portion including an adhesive layer applied to said inner surface of said flap.

6. A urinary diaper or shield as in claim 5, wherein:
   (a) said adhesive layer being covered by a removable protective layer.

7. A urinary diaper or shield as in claim 1, wherein: said flap portion having a width approximately one half the length of said shield.

* * * * *